US008319632B1

(12) United States Patent
Vaisnys et al.

(10) Patent No.: US 8,319,632 B1
(45) Date of Patent: Nov. 27, 2012

(54) SYSTEM AND METHOD FOR MONITORING EXTERNAL PORTABLE MEDICAL DEVICES

(76) Inventors: Gintaras A. Vaisnys, Chicago, IL (US); Giovanni C. Meier, Madison, CT (US); Glenn W. Laub, Princeton, NJ (US)

( * ) Notice: Subject to any disclaimer, the term of this patent is extended or adjusted under 35 U.S.C. 154(b) by 0 days.

(21) Appl. No.: 13/317,702

(22) Filed: Oct. 25, 2011

Related U.S. Application Data

(63) Continuation of application No. 12/229,570, filed on Aug. 25, 2008, now Pat. No. 8,081,071.

(51) Int. Cl.
G08B 21/00 (2006.01)
(52) U.S. Cl. .................. 340/539.12; 340/539.24; 607/5
(58) Field of Classification Search ............ 340/539.12, 340/539.24, 540; 607/5
See application file for complete search history.

(56) References Cited

U.S. PATENT DOCUMENTS

| 5,879,374 A * | 3/1999 | Powers et al. ............. 607/5 |
| 7,570,994 B2 * | 8/2009 | Tamura et al. ............ 607/5 |

OTHER PUBLICATIONS

"On-Off keying" Wikipedia, Nov. 13, 2010.*

* cited by examiner

*Primary Examiner* — Jeffery Hofsass
(74) *Attorney, Agent, or Firm* — William B Gowanlock

(57) ABSTRACT

External portable medical devices, such as portable external defibrillators (PEDs), have long standby times and may be required to indicate their operational status to a user while conserving battery power. Frequently, numerous PEDs are scattered throughout one or more large facility, which may make identifying a PED that is indicating an operational status that requires attention more difficult. To conserve power and provide more effective notice, a PED may use a broadcast transmitter, which minimizes power usage, to communicate the PED's status to a remote monitor that is connected to a relatively unlimited power supply. The remote monitor may then provide a wide variety of sensory alerts to indicate the status of the PED without concern for the power consumption associated with the sensory alert.

32 Claims, 10 Drawing Sheets

SYSTEM AND METHOD FOR MONITORING EXTERNAL PORTABLE MEDICAL DEVICES

CROSS REFERENCE TO RELATED APPLICATIONS

This application is a continuation of U.S. patent application Ser. No. 12/229,570 filed Aug. 25, 2008 now U.S. Pat. No. 8,081,071 and entitled "System and Method for Monitoring External Portable Medical Devices." The complete disclosure of the above-identified application is fully incorporated herein by reference.

TECHNICAL FIELD

The present invention is generally directed to external portable medical devices, and relates more particularly to the remote monitoring of Portable External Defibrillators (PEDs) to provide alerts of conditions on the PEDs while minimizing power consumption from the PED's battery.

BACKGROUND OF THE INVENTION

External defibrillators ("EDs") are emergency medical devices designed to supply a controlled electric shock (i.e., therapy) to a person's heart during cardiac arrest. This electric shock is delivered by pads that are put into contact with the person's body.

During a cardiac arrest, the heart loses its normal electrical rhythm, commonly referred to as cardiac arrhythmia, and may adopt a fibrillation or tachycardia rhythm. As a result, the heart is unable to pump blood properly through a person's body. Unless a timely rescue attempt using an ED is made to restore the normal electrical rhythm, death can result.

To provide a timelier rescue attempt for a person experiencing cardiac arrest, some EDs have been made portable and have been designed to be operated by non-medical personnel. These portable EDs (PEDs) have gained acceptance by those outside the medical profession and have been deployed in myriad locations outside of traditional medical settings. Due to the life saving benefits of PEDs, more and more non-medical users are purchasing and deploying PEDs in their respective environments. This allows for a rescue attempt without the delay associated with bringing the person to a medical facility, or bringing a medical facility to the person (e.g., a life support ambulance).

Individuals as well as businesses are purchasing and deploying PEDs. As time is of the essence during any rescue attempt, multiple PEDs may be purchased by any particular individual or user to allow placement at multiple locations. In the case of an individual, this could be on several floors of a home, and in the case of a business, this could be for placement throughout a facility (e.g., factory, office building, or large retail center). Thus, regardless of where the victim is within the home/facility, access to a PED would only be seconds, or minutes, away.

Many of these deployed PEDs rely on battery power. More specifically, they use a battery as their primary source of power and are stored disconnected from a power grid (e.g., the battery is not constantly being charged). As these PEDs are standby devices that are used infrequently, typically a PED will remain in storage for long periods of time until, if ever, called upon to perform a rescue attempt.

Battery powered PEDs have a fixed battery life (e.g., the batteries must be recharged or replaced after some interval of time). Typically, battery life is measured in terms of months or even years. Minimizing power consumed (i.e., battery drain) by the PED while in storage to maximize PED availability is critical for a rescue attempt. More specifically, battery life is determined by two main factors, battery aging and battery usage. Battery aging results from the ongoing chemical reaction taking place in the battery, thus sets the maximum battery life possible. Battery usage, however, is due to such factors as tasks the PED must perform during storage to assure proper functioning, such as simple maintenance checks, and shortens battery life. It should be appreciated that regardless of the reason, a battery will lose power over time. Unfortunately, if the battery is not serviced there will come a point in the life of a PED where the PED will be unable to provide the necessary life saving shock during a rescue attempt due to a low battery condition.

In addition to battery life issues, PEDs may also have other issues. As mentioned above, the battery may provide power for performing maintenance checks to assure proper functioning. It is thus always possible that the PED may have a maintenance issue that requires action to allow the PED to function properly.

As a result of battery life issues and maintenance issues, a PED may require both scheduled maintenance (e.g., battery replacement) and unscheduled maintenance to assure that it is always ready to provide its life saving therapy when called upon.

To this end, PEDs incorporate various sensory alerts (i.e., devices that the senses (such as eyes or ears, can detect) to notify a user when maintenance is needed. For example, a PED may incorporate mechanical means, such as a status indicator (e.g., a flag that changes colors—from green (i.e., in service) to red (i.e., maintenance needed, or out-of-service)). These types of passive sensory alerts have the benefit of being very low power, but are subtle and can easily be missed, such as when the PED is not stored in plain sight (e.g., in a closet), or in low lighting. Active sensory alerts, such as an auditory (e.g., beeping alarm) or visual (e.g., a flashing light), provide a more noticeable signal, but use much more power.

It should be appreciated that sensory alerts are ideally provided before the PED reaches the point where it cannot function in a rescue attempt, but must be provided when the PED is no longer capable of performing a rescue attempt. It should also be appreciated that sensory alerts, particularly of the active types, depending upon their robustness can use significant battery power. Thus, there is a tradeoff between power usage for sensory alerts that command attention, and retaining power for a rescue attempt. In the most extreme and undesirable situation, a sensory alert meant to indicate simply a need for maintenance to preserve an existing rescue attempt capability (e.g., a low but usable battery) could actually drain sufficient power from the PED battery so the PED would not be able to perform a rescue attempt.

In the rigid and controlled medical environment, PEDs are constantly monitored and checked to assure the PED's operational status, thus low subtle sensory alerts are effective. However, in the less rigid and uncontrolled non-medical environment, the robustness of the sensory alert needed to assure action may use a significant amount of power. Thus, there is a need in the art for a more effective method of monitoring PEDs and alerting those in charge of the PED's maintenance when a PED is in need of maintenance to assure that it is ready to support a rescue attempt when called upon to do so.

SUMMARY OF THE INVENTION

In accordance with the present invention, a portable emergency medical device interacts via a transmitter with a monitor, which is remote from the portable emergency medical device. As a result of the interaction, the monitor can make an assessment of the operational status of the portable emergency medical device, and, if appropriate, alerts a user of its need for service.

More specifically, the portable emergency medical device has self-diagnostic tests that determine the operational status of the device. These self-diagnostic tests, which may be activated sua sponte, are capable of determining, for example, whether the portable emergency medical device is ready to perform its function or not. Based on the outcome of the self-diagnostic tests, the portable emergency medical device communicates its operational status to a user by transmitting a signal to the monitor.

One feature of the present invention is to provide a remote capability to assess and notify a user of the operational status of a battery powered portable emergency medical device using as little battery power of the portable emergency medical device as possible. As a result, battery power of the portable emergency medical device is conserved for a rescue attempt. In addition, the monitor, which has a power supply independent of the portable emergency medical device, can have sensory alerts that are considerably more robust than those in a portable emergency medical device. Further, the monitor can be located in an area more favorable to a user detecting and acting upon an alert from a sensory alert.

Other features, attainments, and advantages will become apparent to those skilled in the art upon a reading of the following descriptions when taken in conjunction with the accompanying drawings.

DETAILED DESCRIPTION OF EXEMPLARY EMBODIMENTS

The term "portable emergency medical device" as used herein means a medical device intended by its design to be readily movable (e.g., carried) by a typical human being of ordinary strength, and to be a self-contained medical device (e.g., has an integrated portable power source (e.g., battery, crank generator)), which performs a medical procedure (e.g., a defibrillator) that is stored in a location, such as on a shelf or in a closet, and for use is retrieved and associated with a body, such as that of a human, to perform the medical procedure for which it was created. The term "broadcast transmitter/receiver combination" as used herein means a broadcast transmitter and broadcast receiver that work in combination that need not be collocated, but are not as a precondition to transmitting and receiving data required to establish first their mutual co-existence and compatibility (e.g., Wi-Fi and Bluetooth). Thus all things being equal, a broadcast transmitter transmits its data consuming less power from a power source.

Common examples of broadcast transmitter/receiver combinations are radio transmitters and radios, television transmitters and televisions, and generally most remote control devices and the device they control (e.g., television remotes and televisions). A common feature of broadcast transmitter/receiver combinations is that the broadcast transmitter upon an initiating transmission does not transmit to a known, particular broadcast receiver, or know if any broadcast receiver is within range.

It is possible, that a second receiver associated with a broadcast transmitter may receive a confirmation transmission from a second transmitter associated with the broadcast receiver to indicate that the broadcast transmitter should continue broadcasting, or indicate a successful transmission. A common example of this is a walkie-talkie wherein a first walkie-talkie makes an initial transmission using its broadcast transmitter and then waits for a second walkie-talkie to respond, indicating its presence, before making another transmission and so on.

The term "battery" as used herein means a cell (e.g., a D cell) or group of cells (e.g., two D cells in series) for providing power.

Figure 1:
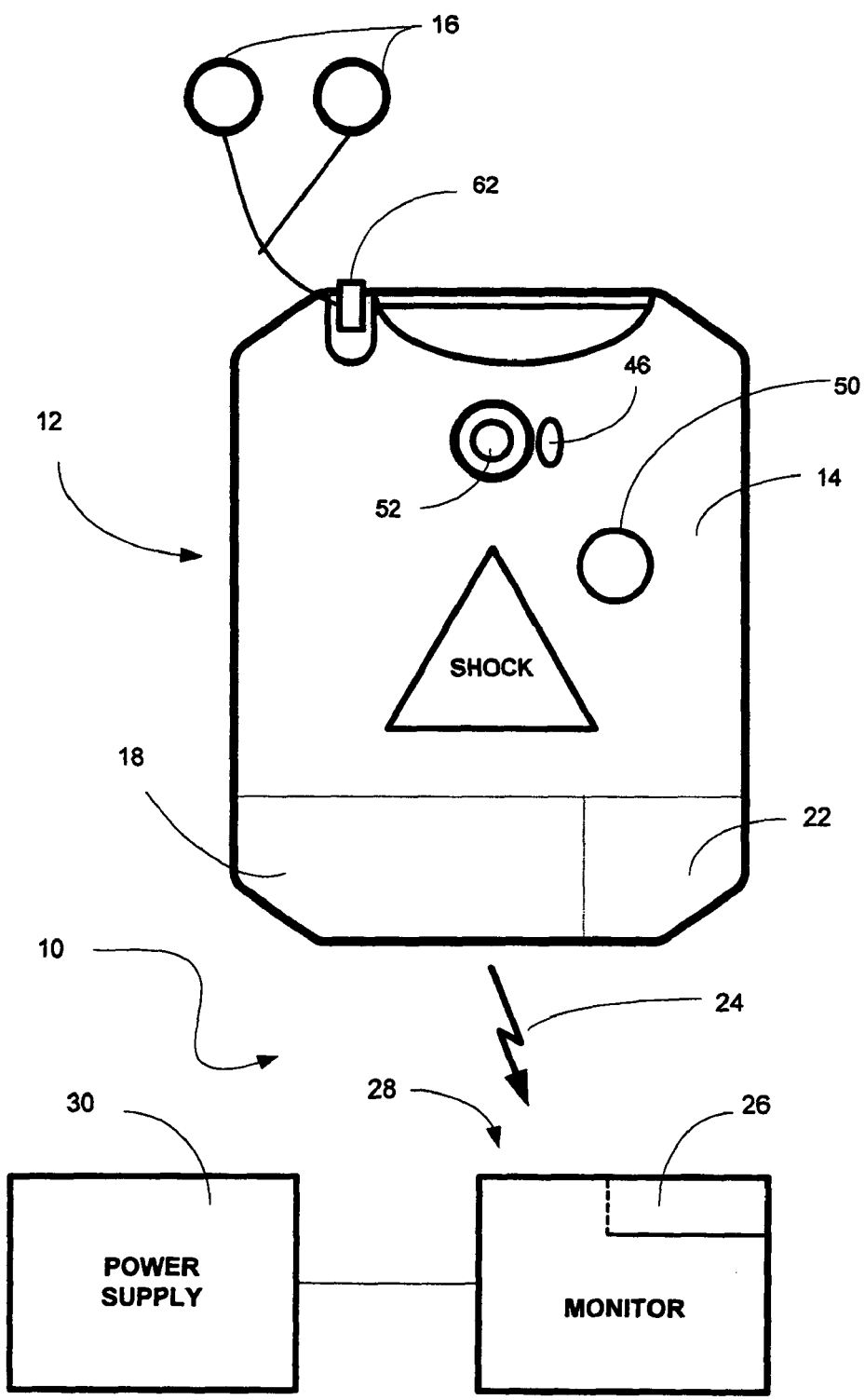
FIG. 1 illustrates a plan view of a system for monitoring a PED according to one exemplary embodiment of the invention.

Turning now to the drawings, FIG. 1 illustrates a system for monitoring a portable emergency medical device (generally referred to by reference number 10) which includes a portable emergency medical device 12 (illustrated as and hereinafter referred to as a Portable External Defibrillator (PED)). A PED 12 generally includes a base unit 14, having the necessary programmable circuitry for performing the medical procedure of the PED (well known to those skilled in the art), and a set of pads 16 associated therewith. For this particular PED 12, the pads from the set of pads 16 are appropriately placed on a body (not shown) and an electrical shock generated in the base unit 14 is passed through the body when the "SHOCK" button is depressed. Within the base unit 14, is a battery 18 for powering the PED 12 and a broadcast transmitter 22 of a broadcast transmitter/receiver combination.

The system 10 further includes a broadcast receiver 26, which is the receiver of the broadcast transmitter/receiver combination. The broadcast transmitter 22 transmits a condition information stream 24 to the broadcast receiver 26 that is in a monitor 28. The monitor 28 is remote from the PED 12.

The monitor 28 is powered by a power supply 30, which is independent of the PED's battery 18. Therefore, the battery 18 of the PED 12 is not powering the monitor 28. As a result, the power available to the PED 12 from its battery 18 is not altered by the power consumed by the monitor 28. It should, therefore, be appreciated that where the PED 12 is attached to a power grid (e.g., for battery charging) and the monitor 28 is attached to the same power grid, the two power supplies would still be considered independent within the context of this invention, as the operation of one does not change the power available to the other.

Figure 2:
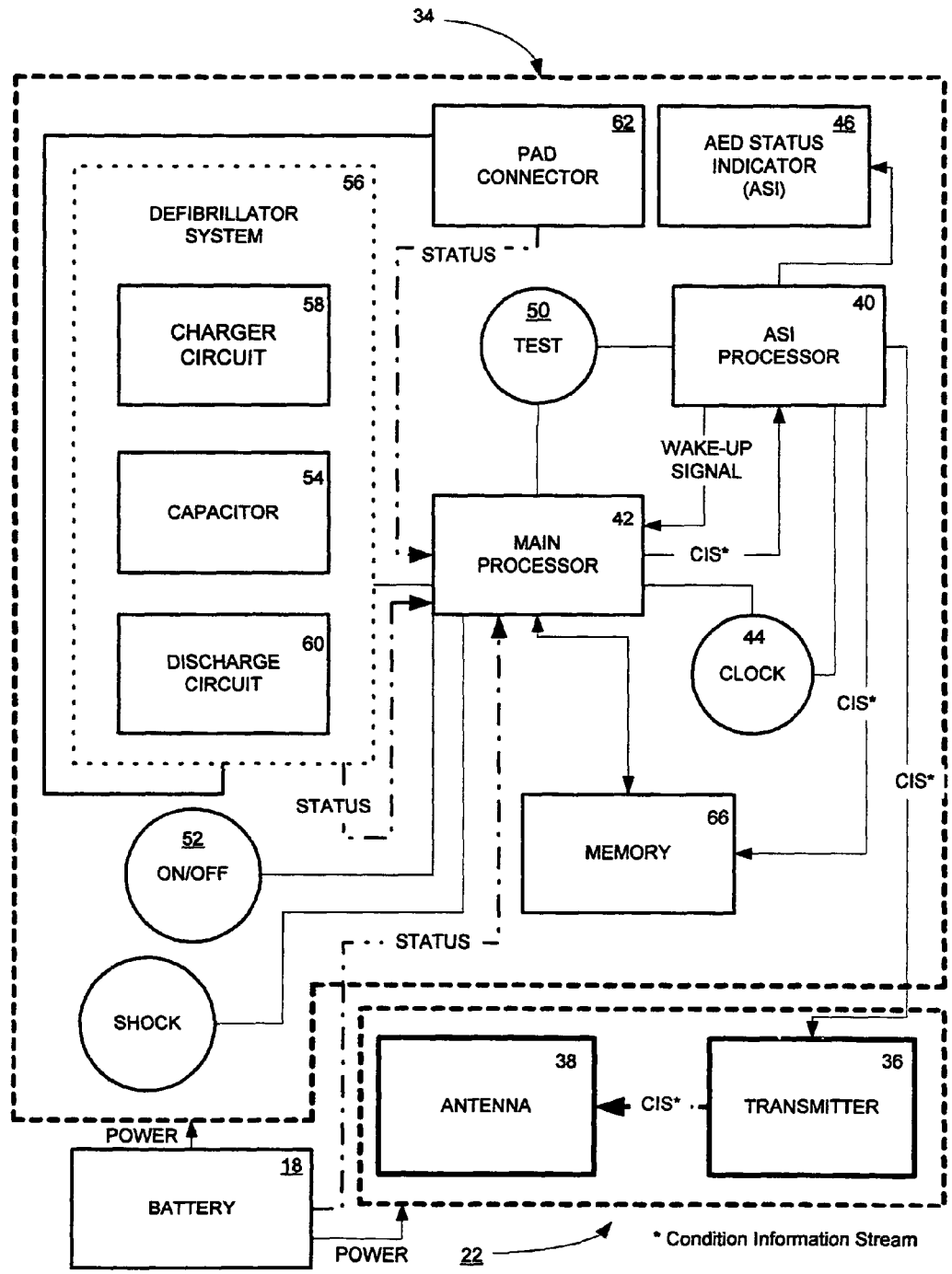
FIG. 2 is a functional block diagram illustrating a PED which is part of the system according to one exemplary embodiment of the invention.

FIG. 2 is a block diagram of the PED 12. Underlined reference numbers indicate structure depicted in FIG. 1.

As shown in FIG. 2, the broadcast transmitter 22 is electrically connected to the PED's 12 programmable circuitry 34. As illustrated, the broadcast transmitter 22 includes a transmitter 36 connected to an antenna 38.

The broadcast transmitter 22 may be capable of generating a signal of constant frequency and amplitude, so that when it is turned "on" then "off" and back "on" the same signal is produced. A transmitter that may be used with the present invention is an Elsie RF transmitter. The Elsie RF transmitter includes a Surface Acoustic Wave (SAW) stabilized Colpitts oscillator with a carrier frequency of 433.92 MHz. As those skilled in the transmitter design arts will appreciate, depending on the geographical location where the transmitter is to be utilized and the range of the transmitter, governmental regulations may dictate which frequencies may be used.

In this illustrative example, the broadcast transmitter 22 is controlled by an active status indicator (ASI) processor 40 of the programmable circuitry 34. The ASI Processor 40 cooperates with a Main Processor 42, of the programmable circuitry 34, to conduct and then report the results of at least some self-diagnostic test of the PED 12.

More specifically, the PED 12 has a STANDBY mode, a MANUAL-TEST mode, an AUTO-TEST mode, and an ON mode. The MANUAL-TEST mode, AUTO-TEST mode, and ON mode may all have self-diagnostic testing to determine the capability of the PED 12 programmable circuitry 34 to perform a rescue attempt. The STANDBY mode is the lowest energy consuming mode.

In the STANDBY mode, the PED 12 has a running clock 44 and an active status indicator (ASI) 46. As illustrated, the clock 44 is associated with the ASI Processor 40. The ASI 46 indicates, in this case by solid or blinking green or red lights, the last known operational status (e.g., ready with no maintenance needed, ready but maintenance needed, not ready) of the PED 12. The ASI 46 is controlled by the ASI Processor 40.

The PED 12 may be automatically put into the AUTO-TEST mode from the STANDBY mode sua sponte (i.e., as a result of its own action) by the PED. The PED 12 may go into AUTO-TEST mode periodically (e.g., when a time interval is reached). More specifically, in this illustrative example in the STANDBY mode the clock 44 maintains time and causes the ASI Processor 40 to come "on" at a fixed interval, to accomplish the routine task of operating the ASI 46.

Programming in the ASI Processor 40 tracks the number of "on" intervals and when a sufficient number is accumulated sends a "wake-up" signal 48 to the Main Processor 42; thereby beginning the AUTO-TEST mode. Upon receiving the "wake-up" signal 48, the Main Processor 42 is powered and programming in the Main Processor determines the time from the clock 44, and based on that time determines the self-diagnostic test required and then performs the self-diagnostic test. At the end of a self-diagnostic test, programming in the Main Processor 42 puts the PED 12 back into the STANDBY mode.

In order to minimize battery power consumption during the AUTO-TEST mode, different self-diagnostic tests may be performed at different times. For example, there may be daily, weekly, monthly, and quarterly self-diagnostic tests. As those skilled in the art appreciate, to maximize battery life there should be an inverse relationship between the frequency of a self-diagnostic test and the power it consumes. Thus, a daily self-diagnostic test should consume less power than a weekly self-diagnostic test and so on.

As stated above, the self-diagnostic tests vary to balance effective self-diagnostic testing of the PED 12 and PED battery 18 life. For example, the daily self-diagnostic test may include powering up the Main Processor 42 to check software integrity, basic operation of electronic circuitry, and pad presence. The weekly self-diagnostic tests could add such elements to the daily self-diagnostic test as advanced circuit and battery integrity, broadcast transmitter integrity, patient interface circuitry, defibrillation electrode analysis, and capacitor/discharge circuit evaluation using partial charging. The monthly self-diagnostic tests could add to weekly self-diagnostic test discharge at the partial charge. The quarterly self-diagnostic test could add to the monthly regimen a simulated full ON condition with discharge.

In the MANUAL-TEST mode, which is activated by a user, a user activates a self-diagnostic test. Depending upon the sophistication of the PED 12, the user may be able to select a particular self-diagnostic test from a selection of self-diagnostic tests. A check pad self-diagnostic test can be activated by depressing a test button 50. Where there is only a single self-diagnostic test available in the MANUAL-TEST mode, it should test as much of the PED 12 as possible, including but not limited to charging and discharging (internally only). The self-diagnostic test(s) available in the MANUAL-TEST mode may be the same as those in other modes.

When the PED 12 is put into ON mode, the PED has a power-on self-diagnostic test, which may be the same as a self-diagnostic test in other modes. In this illustrative example, the ON mode is manually activated by an ON/OFF Button 52. When the ON/OFF Button 52 is in the ON position, the PED 12 prepares to give a patient a shock by activating all the necessary circuits, and performing the power-on self-diagnostic test to determine availability to perform the rescue mission. It should be appreciated that to effectuate a rescue, charging of a capacitor 54, which is part of the PED's defibrillator system 56 that is part of the programmable circuitry 34, will be required. When and how the capacitor 54 is charged is well known in the art. The defibrillator system 56 further includes a charger circuit 58 and a discharge circuit 60.

When a self-diagnostic test is performed, data obtained from the self-diagnostic test may be transmitted by the broadcast transmitter 22 to the broadcast receiver 26 in the condition information stream 24. It is not necessary that every time a self-diagnostic test is performed a condition information stream 24 be generated, or, if generated, be transmitted.

As shown in FIG. 2, the condition information stream 24 may be created by the ASI Processor 40 or the Main Processor 42. If created by the Main Processor 42, the Main Processor may obtain input from itself, the battery 18, the defibrillator system 56, the pad connector 62 and the memory 66, depending upon the self-test preferred. Generally, the ASI Processor 40 generates a condition information stream 26 when the Main Processor 42 fails to provide a timely condition information stream 24 to the ASI Processor 40. As a means of assuring the condition information stream 24 is not lost, the ASI Processor 40 may also send a copy of it into memory 66.

Figure 3:
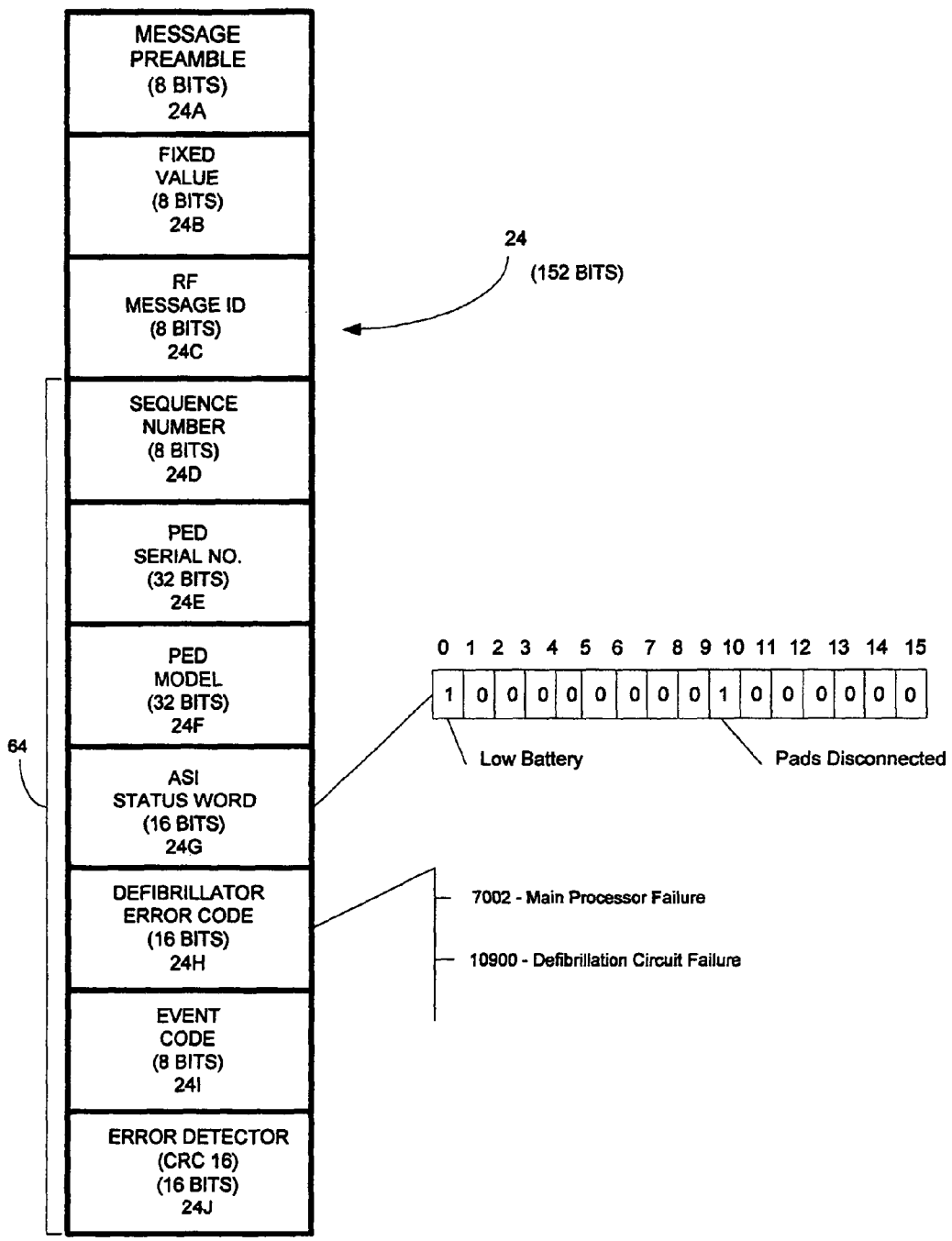
FIG. 3 is an exemplary condition information data stream.

As illustrated in FIG. 3, the condition information stream 24 may have several parts. In this illustrative example, the condition information stream 24 is 152 bits in length and includes a message preamble 24A of 8 bits, a fixed value 24B of 8 bits, an RF message ID 24C of 8 bits, and a data payload 64.

The data payload 64 may include a unique sequence 24D of 8 bits, a PED Serial No. 24E of 32 bits, a PED Model No. 24F of 32 bits, an ASI status word 24G of 16 bits, a defibrillator error code 24H of 16 bits, an event code 24I of 8 bits, and an error detector 24J of 16 bits. As those skilled in the art will appreciate, the illustrated condition information stream 24 is but one example, however, the data payload as used herein means that part of the condition information stream contains at least some data that may change to indicate a change in the operational status (e.g., out-of-service) of the PED 12.

The message preamble 24A may be a series of bits, generally all the same (e.g., 1s or 0s). The message preamble 24A provides the time and signal necessary for programming in the monitor 28 to set the broadcast receiver 26 thresholds to receive the balance of the incoming condition information stream 24. It is not necessary that the broadcast receiver 26 receive the entire message preamble 24A, or that each bit of the message preamble be properly framed (i.e., interpreted).

The fixed value 24B is a predetermined, known series of bits that provides a framing reference. In other words, the fixed value 24B provides a means for programming in the monitor 28 to determine how to begin reading the condition information stream 24 by providing a known value, and also may identify the data stream as being relevant to the monitor 28. In other words, the broadcast receiver 26, thus the monitor 28, is always waiting to receive a condition information stream 24. Thus, any data stream on the broadcast receiver's 26 frequency will be detected by the broadcast receiver, and the monitor 28 needs a means to determine if it is a condition information stream 24. The Message ID 24B may be an 8 bit word, such as a "D."

The RF Message ID 24C is a value that assists in the differentiation of data payloads. More specifically, the RF Message ID 24C defines the digital format of the data payload 64 of the condition information stream 24. The data payload 64 of the condition information stream 24 contains some number of bits that must be subdivided to extract information, and the monitor's 28 programming must know the format. For example, the RF Message ID 24C could be 8 bits that translate into a word, such as "S." An "S" indicates a data payload 64 having an "S" structure. The "S" structure, which would be known by the monitor's 28 programming, could mean the unique sequence 24D, discussed below, is 8 bits, the PED Serial Number 24E, discussed below, is 32 bits, etc. A change in RF Message ID 24C would indicate a change in the number of bits or how the bits are partitioned within the data payload 64.

The unique sequence 24D is a unique value for each condition information stream 24 from a given broadcast transmitter 22. The unique sequence 24D provides the ability for the monitor's programming to differentiate condition information streams 24 from a given broadcast transmitter 22, thus PED 12.

Where the unique sequence 24D is an ordered value known to the monitor's 28 programming, the unique sequence 24D can be used to place the various condition information streams 24 from a PED 12 in order. It could also be used by the monitor's 28 programming to determine if a particular condition information stream 24 was not collected by the monitor 28; thus, an alert should be issued. Typically, ordered values are well known ordinal schemes, such as 1, 2, 3, etc.

The unique sequence 24D may provide the monitor's 28 programming the ability to determine if it missed receiving a particular condition information stream 24.

The PED Serial No. 24E is a unique identifier of a particular PED 12. The PED Serial No. 24E is generally assigned by the manufacturer.

The PED Model No. 24F is an identifier that relates a PED 12 to a particular group of PEDs. The PED Model No. 24F is assigned by the manufacturer.

The PED Status Word 24G identifies an operational condition of a PED 12. A reasonable PED Status Word 24G is best read as a status bit field. More specifically, the PED Status Word 24G has 16 bits numbered 0-15. Each bit can have a 1 or 0 status, and each bit can be associated with a particular issue. For example, bit 0 could be related to primary battery condition. If it is a 0 the primary battery is fine, if 1, the primary battery is low. Similarly, for bit 6, a 0 could indicate pads connected, while a 1 could indicate no pads connected.

The defibrillator error code 24H provides a code relevant to an identified failure. In this example, the defibrillator error code 24H is 16 bits, which can potentially provide up to 65,565 error codes.

Taken together, or individually, the PED Status Word 24G and the defibrillator error code 24H provide operational status information, which may generate an alert. This is discussed in detail below.

The event code 24I indicates the event, e.g., AUTO-TEST, MANUAL TEST, or ON, that generated the condition information stream 24.

The error detector 24J provides a check (e.g., CRC16) of some or all the data within the condition information stream 24. More specifically, the error detector 24J is constructed from all, or some, of the information in the condition information stream 24. Generally, the Message Preamble 24A will be excluded. The error detector 24J provides a means for the monitor's 28 programming to check the content of the condition information stream 24 for accuracy of receipt.

It should be appreciated that some of the contents of the condition information stream 24 (e.g., defibrillator error code 24H) are generated based on self-diagnostic test results. Therefore, there is no requirement that all condition information streams 24 from a PED 12 be the same. And as used herein, the phrase "condition information stream" when used in conjunction with a PED includes the limitation that all condition information streams 24 from a PED are not required to be the same.

To facilitate data transfer, the condition information stream 24 may use a known coding scheme. One possible coding scheme is Manchester Coding. Manchester coding (also referred to as Phase Encoding, or PE) is a line code coding scheme in which the encoding of each data bit (e.g., 1 or 0) has at least one transition and occupies the same time duration (i.e., has the same time duration). As a result, this type of line code is considered self-clocking (e.g., the clock signal can be recovered from the encoded data). Thus, the condition information stream 24 does not need to have a separate clock signal.

Manchester coding can be achieved by essentially turning the broadcast transmitter 22 (See FIG. 2), more specifically the transmitter 36, "on" and "off." This procedure is commonly referred to as On-Off Keying (OOK) or Amplitude Shift Keying (ASK). When this is done, the frequency and amplitude of the signal from the broadcast transmitter 22 may remain constant.

The distance over which data can be transmitted, all other conditions being the same, is inversely related to baud rate at which the message is sent. The ability to decode accurately the condition information stream 24 can be increased by incorporation of a return-to-zero (RZ) data code.

Turning the broadcast transmitter 22 "on" and "off" to send the condition information stream 24 minimizes battery usage. Since the broadcast transmitter 22 is only "on" to send some portion of the condition information stream 24, a majority of the time the broadcast transmitter 22 is not powered. This approach, thus, uses minimal battery power.

The broadcast transmitter 22 may operate on a different schedule than the schedule for self-diagnostic tests. For example, the self-diagnostic tests may run every hour with the broadcast transmitter 22 transmitting only once in a 24 hour period, as long as the status of the PED 12 is acceptable. Ideally, the broadcast transmitter 22 should transmit immediately if a problem has been detected.

As a practical matter, when the broadcast transmitter 22 is operated, the condition information stream 24 could be transmitted several times at fixed or random intervals. Multiple transmission are particularly important to avoid collisions between conditions information stream 24 from multiple PEDs 12 that are being monitored by a single monitor (this case is discussed below). This multiple transmission gives the broadcast receiver 26 in the monitor 28 several opportunities to receive the transmission. It should be appreciated that if a problem has been detected the transmission could be more frequent in time and more robust in energy.

Figure 4:
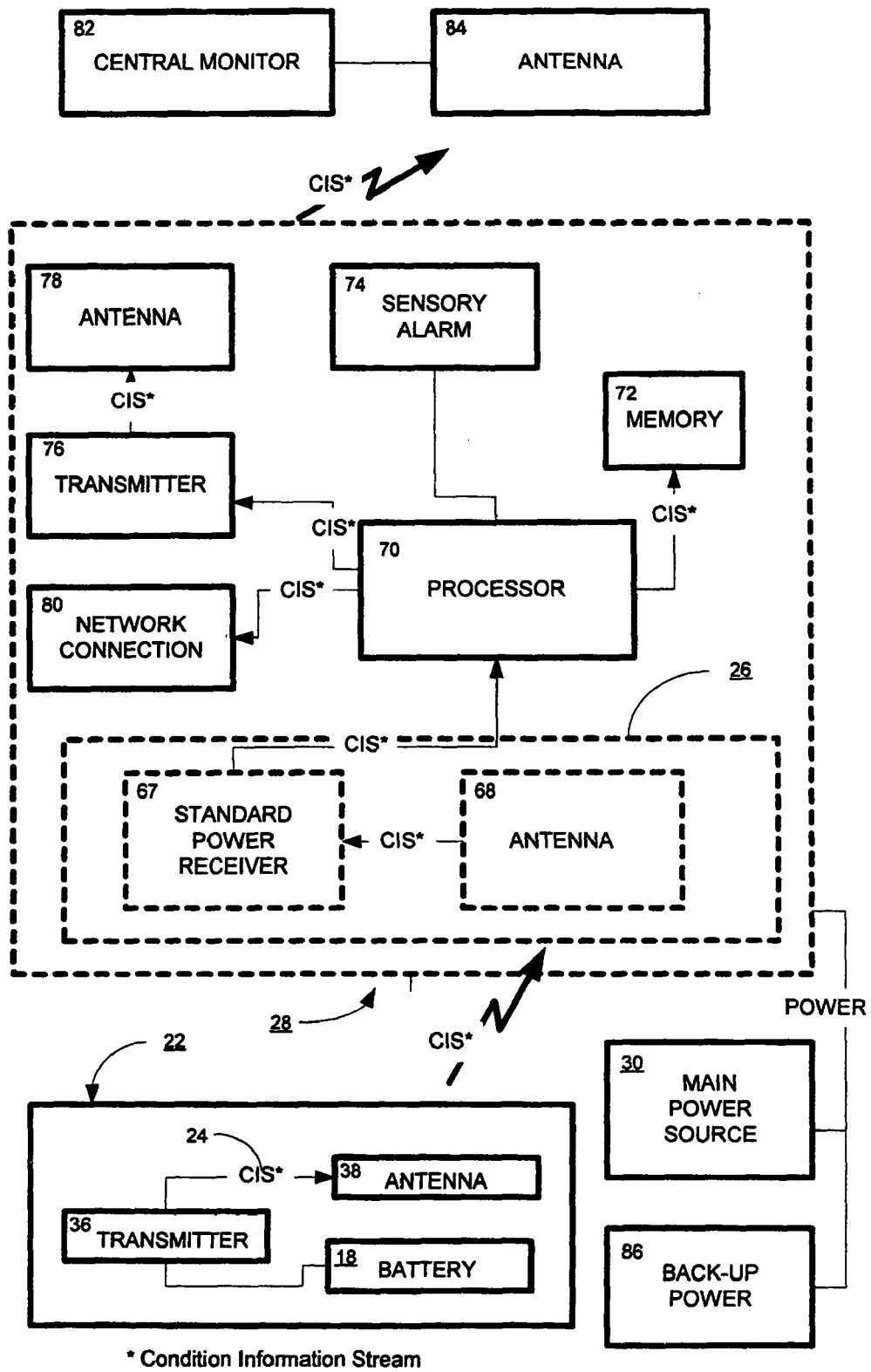
FIG. 4 is a functional block diagram illustrating a remote monitor of the system according to one exemplary embodiment of the invention.

FIG. 4 is a block diagram of the monitor 28 and the transmitter 22 depicted in FIG. 1 interacting with a central monitor. Underlined reference numbers indicate structure depicted in FIG. 1.

Referring to FIG. 4, the monitor 28 contains the broadcast receiver 26, having a receiver 67 which is connected to an antenna 68, and programmable circuitry, having a processor 70 associated with memory 72. The broadcast receiver 26 is capable of receiving a condition information stream 24 from the broadcast transmitter 22 within a PED 12. The processor 70 contains programming to decode the condition information stream 24 and act upon the information contained therein.

The monitor 28 may also include a sensory alert 74, a transmitter 76 connected to antenna 78, and a network connection 80. The sensory alert 74 can be of almost any type of sensory alarm, such as visual or audible device. It should be remembered that the monitor 28 is utilizing a main power source 30 that is separate from the battery 18 of the PED 12. Ideally, the monitor 28 is plugged into a constant ON power grid (e.g., in the US a standard 120v outlet). Thus, the sensory alert 74 can be as robust as desired to get the attention of personnel (e.g., maintenance personnel) without worry that the battery 18 of the PED 12 is being drained.

The sensory alert 74 may have one or more sensory alarms (i.e., output devices that at least one of the senses of a human can detect) for getting the attention of a human. For example, the sensory alarms devices may include speakers for generating sounds (e.g., commands such as "action required," or noise), horns (e.g., beeping sounds), lights (e.g., blinking lights or solid colors), or mechanical devices (e.g., flags to be deployed upon detection of a problem). As the monitor 28 is connected to the main power source 30 that will not affect the power available to the PED 12, these sensory alarms may be quite robust.

In addition, the monitor 28 could include a network connection 80 for incorporating the monitor into an intranet or internet. In addition, the monitor 28 could include a transmitter 76, with antenna 78, for transmitting condition information, or merely an alarm condition, to a central monitor 82, having its own antenna 84. It is possible that the transmitter 76, with antenna 78, could be a cell phone and the central monitor 82, with antenna 84, could be a cell phone. It is certainly possible that a standard transmitter/receiver combination could be used.

The monitor's broadcast receiver 26 is ideally constantly on and ready to receive a condition information stream 24 from a broadcast transmitter 22. The monitor 28 therefore needs a reliable power source (e.g., main power source 30 being a power grid), but it may have backup power 86.

In operation, the transmitter 24 is operated to send a condition information stream 24 as a result of a self-diagnostic test. Generally, the condition information stream 24 will be sent as part of the PED 12 turn off routine. In the ON mode, however, the condition information stream 24 maybe sent at anytime from immediately after the test is performed until a turn off routine is encountered.

As an initial matter, the broadcast receiver 26 would receive notice that the broadcast transmitter 22 is active by receiving the message preamble 24A. The message preamble 24A would allow programming in the monitor 28 to adjust the broadcast receiver 26 gain to receive the balance of the condition information stream 24. The balance of the condition information stream 24 would then be received. If the condition information stream 24 were being sent multiple times, the broadcast receiver 26 would receive all condition information streams.

The monitor's processor 70, which is part of the monitor's circuitry, contains programming to process the condition information stream 24 to extract and analyze the data contained therein. As part of the analysis, the PED Status Word 24G and defibrillator error code 24H would be analyzed to determine if an alert using the sensory alert 74 is needed to alert a person that the PED needs attention. More specifically, the programming should be able to distinguish between those PED Status Words 24G and defibrillator error codes 24H that require an alert due to a PED condition and those which were reporting that the PED is in operating order, which generally would not generate an alert.

The monitor's processor 70 may also contain programming to determine the failure to receive a condition information stream 24. More specifically, the self-diagnostic system of the PED 12 may be designed to perform periodic checks of the PED. In addition, it may be designed to transmit periodically the results of those checks to the monitor 28. Thus, the processor 70 of the monitor 28 could be programmed to recognize when a periodic transmission of a condition information stream 24 was missed based on when it was to occur, recognize when a condition information stream has not been received within a given time period, or analyze the unique sequences 24D within various condition information streams to determine if a specific condition information stream was missed. Ideally, the processor 70 of the monitor 28 would have the ability to learn when the next transmission was expected and await its arrival. This could be accomplished by providing the monitor 28 with the periodic interval and then initializing the monitor with a first condition information stream 24.

Figure 5:
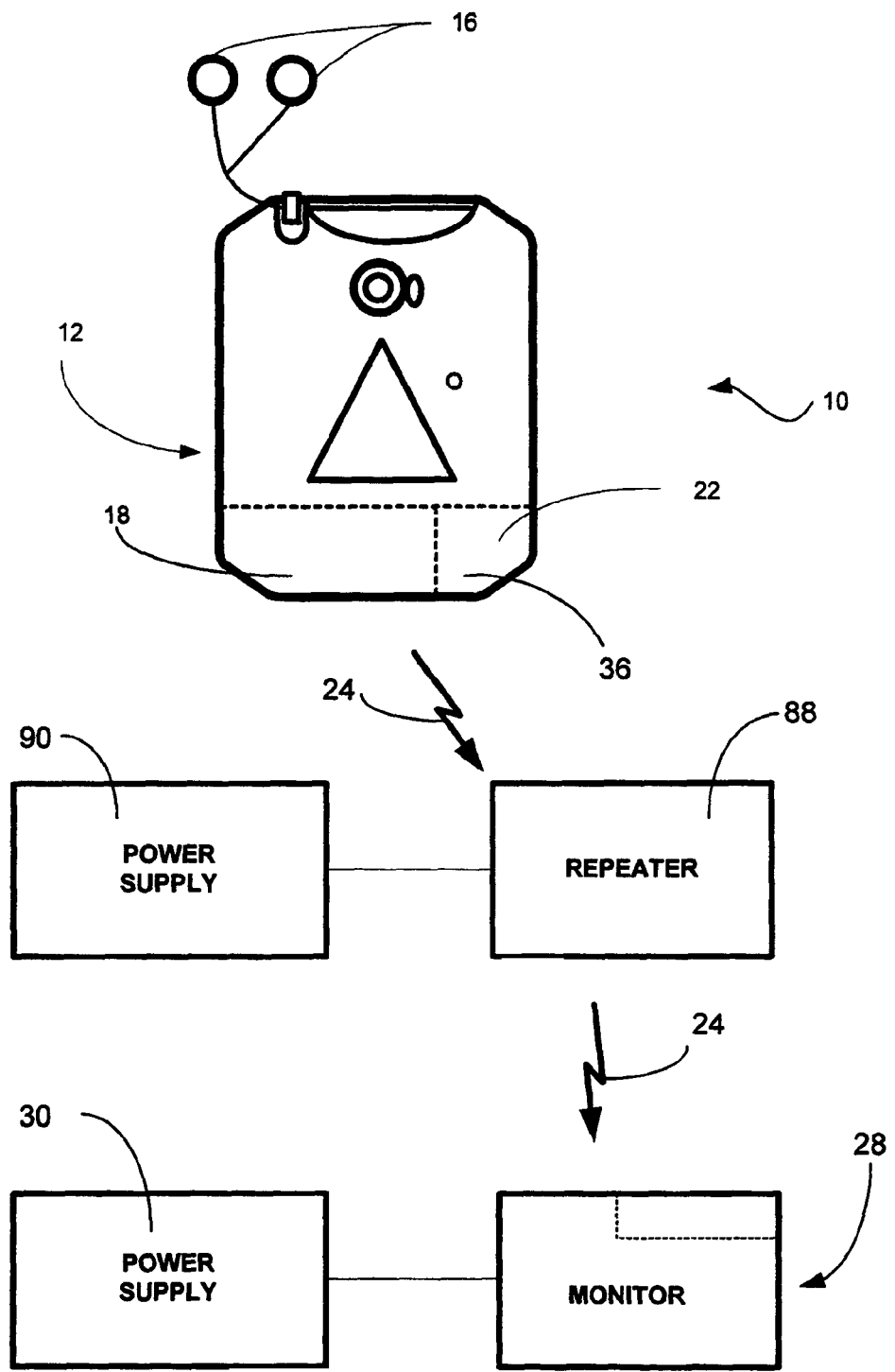
FIG. 5 illustrates a plan view of the system of FIG. 1 incorporating a repeater.

Referring to FIG. 5, the system 10 in addition to a PED 12 and monitor 28 may include a repeater 88. As discussed above, there is a trade-off of power usage (i.e., battery) by the PED's broadcast transmitter 22 and the range of that transmitter. Thus, requiring the monitor 28 to be remote from, but close enough to, the PED 12 to receive the condition information stream 24. This distance, however, can be increased by the use of a repeater 88.

It should be appreciated that the system 10 could further include any number of repeaters 88. More specifically, the range of the broadcast transmitter 22 is limited by the power drain on the PED battery 18 one wishes to tolerate. Thus, repeaters 88 attached to independent power sources 90 could be used to extend the distance between a PED 12 and its associated monitor 28.

Figure 6:
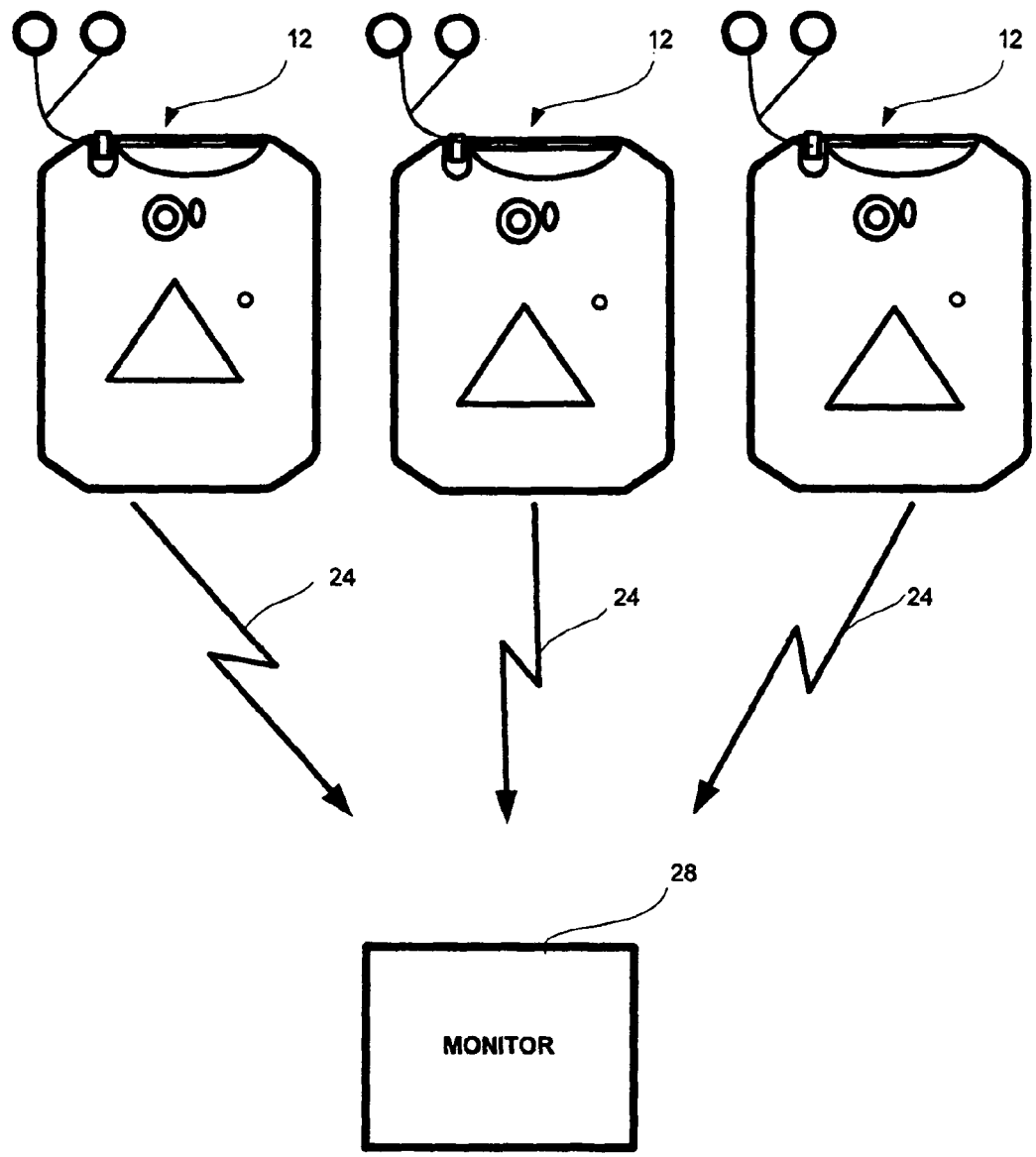
FIG. 6 illustrates a plan view of a system having multiple PEDs being monitored by a single monitor.

As shown in FIG. 6, multiple PEDs 12 may be associated with a single monitor 28. As those skilled in the art will appreciate, if one monitor 28 is monitoring several PEDs 12 the monitor should be able to distinguish between PEDs and identify the relevant PED. More specifically, if the monitor 28 receives a condition information stream 24 from a particular PED 12 indicating a problem, the monitor should be able to indicate the specific PED with the problem. There are many ways to accomplish this objective. The most straightforward method is to use the PED Serial Number 24E in the condition information stream 24 (see FIG. 3).

Figure 7:
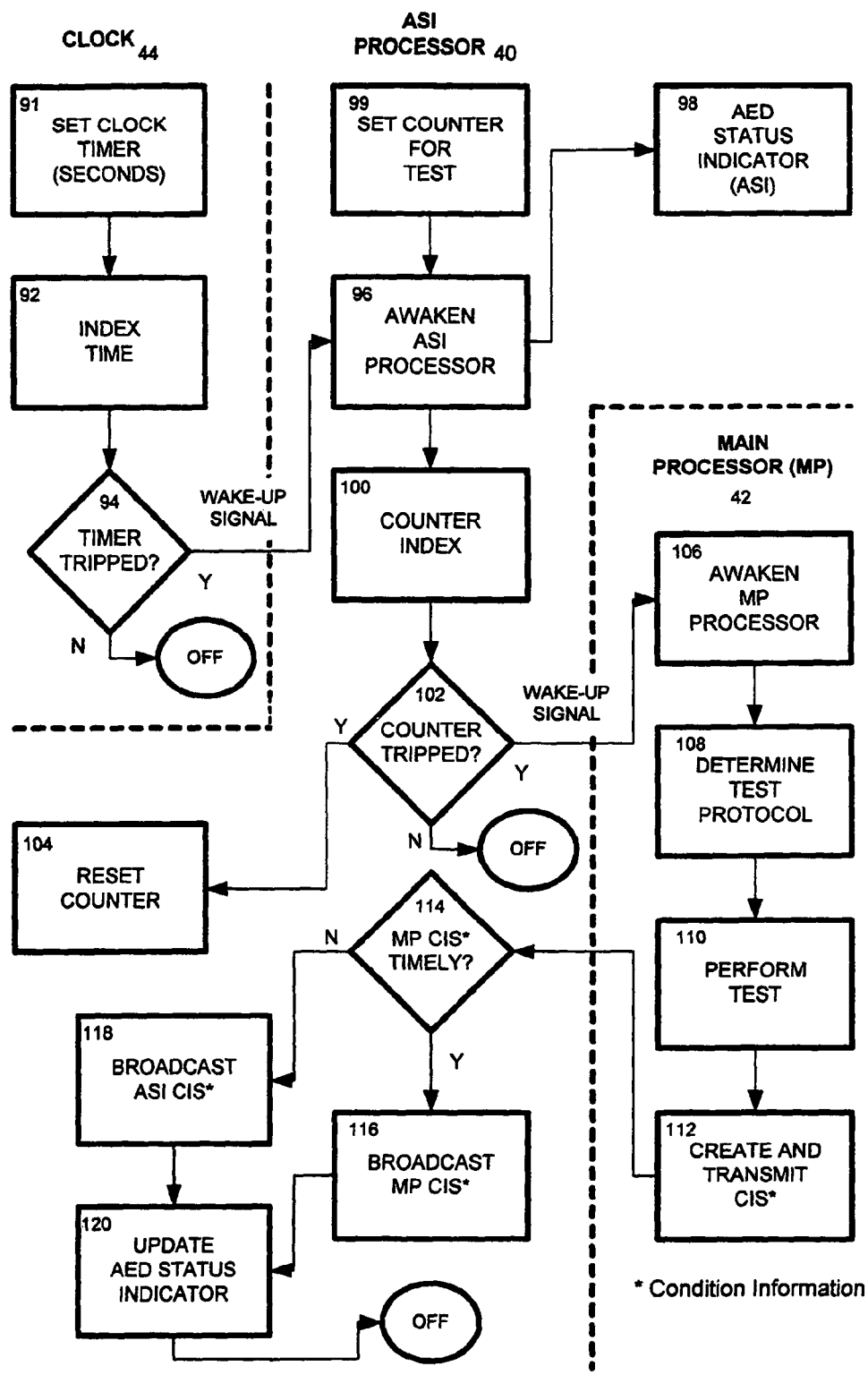
FIG. 7 is a logic flow diagram illustrating exemplary steps for generating a condition information stream according to one exemplary embodiment of the invention.

FIG. 7 shows a method for generating a condition information stream 24 for a PED 12. As shown in FIG. 2, the PED 12 includes a clock 44, an ASI Processor 40, and a Main Processor 42.

Continuing with FIG. 7, the clock 44 contains a timer, step 91, which when activated sends a "wake-up" signal to the ASI 40. More specifically, the clock 44 is programmed with a baseline time and then one second intervals are generated. The timer, step 91, is set to a given number of seconds (e.g., 5). As time passes and is recorded in the time index, step 92, the time index is evaluated, step 94, to determine if the timer should be activated. At the appointed interval (e.g., 5), the timer activates and sends a "wake-up" signal to the ASI Processor 40.

When the ASI Processor 40 is awakened, step 96, the ASI Processor 40 commands the ASI 46, step 98, to display as required based on the last self-diagnostic test. Also, the ASI Processor 40 has programming which contains a counter for self-diagnostic testing, step 99, which may have a fixed value. More specifically, the counter for self-diagnostic testing, step 99 determines when the ASI Processor 40 should send a "wakeup" signal to the Main Processor 42. When the "wake-up" signal is sent is determined by the counter for self-diagnostic testing. For example, if a daily self-diagnostic test is desired, the fixed value of the counter for self-diagnostic testing assuming that the ASI is awakened every 5 seconds is 17,280, calculated as follows—86,400 seconds/day divided by 5 seconds. Thus, every time the ASI Processor 40 is turned "on," a counter index, step 100, is advanced one, and the new counter index is compared to the counter for self-diagnostic test to determine if the counter has be tripped, step 102. If the two values are equal, the ASI Processor 40 sends a "wake-up" signal to the Main Processor 42 and the counter index is reset, step 104. It should be appreciated that the ASI Processor 40 turns itself "off" after performing its ASI 46 function, step 98, if no "wake-up" signal is sent to the Main Processor 42.

If a "wake-up" signal is sent to the Main Processor 42, the Main Processor is powered up, step 106. Upon power up, the Main Processor 42 obtains from the clock 44 the baseline date and the present number of cumulative seconds from the baseline date, step 108. Further, in step 108 using a calendar algorithm, the Main Processor 42 determines the date. Using this date, the Main Processor 42 programming identifies the proper self-diagnostic test. As mentioned above, the PED 12 may contain several self-diagnostic tests, such as daily, weekly, monthly, or quarterly. Based on the date and programming within the Main Processor 42, the Main Processor selects the appropriate self-diagnostic test for the date and performs the self-diagnostic test, step 110.

After completion of the self-diagnostic test, step 110, the programming of the Main Processor 42 creates an appropriate condition information stream 24 and sends that CIS to the ASI Processor 40, step 112. To maximize the chances of receipt by the broadcast receiver 26, the condition information stream 24 may be sent multiple times over a short time period (e.g., one-half hour). Multiple times are prudent because of potential interference from, for example, other PEDs reporting, or failure of the PED to receive the entire message. Where a single condition information stream 24 is sent multiple times, there is a potential it will be received multiple times. The monitor's programming should be able to determine if the same condition information stream 24 has been received multiple times by evaluating the unique sequence 24D. In addition, the programming of the monitor 28 should be capable of taking partial condition information streams 24 which it can identify as being a single information stream and constructing the single information stream.

When the counter index is tripped, step 102, to send a "wake-up" signal to the Main Processor 42, the ASI Processor's 40 programming begins waiting for a condition information stream 24 from the Main Processor, step 114. More specifically, the ASI Processor 40 sets a time limit of receiving a condition information stream 24 from the Main Processor 42. If the Main Processor 42 sends a condition information stream 24 within this time period, the ASI Processor 40 will broadcast the condition information stream 24 from the Main Processor, step 116. In the event, the ASI Processor 40 does not receive a timely condition information stream 24 from the Main Processor 42, the ASI Processor 40 will generate a condition information stream 24 and broadcast that condition information stream, step 118. As a result of the condition information stream broadcast, programming in ASI Processor 40 will update the ASI 46, step 120.

Figure 8:
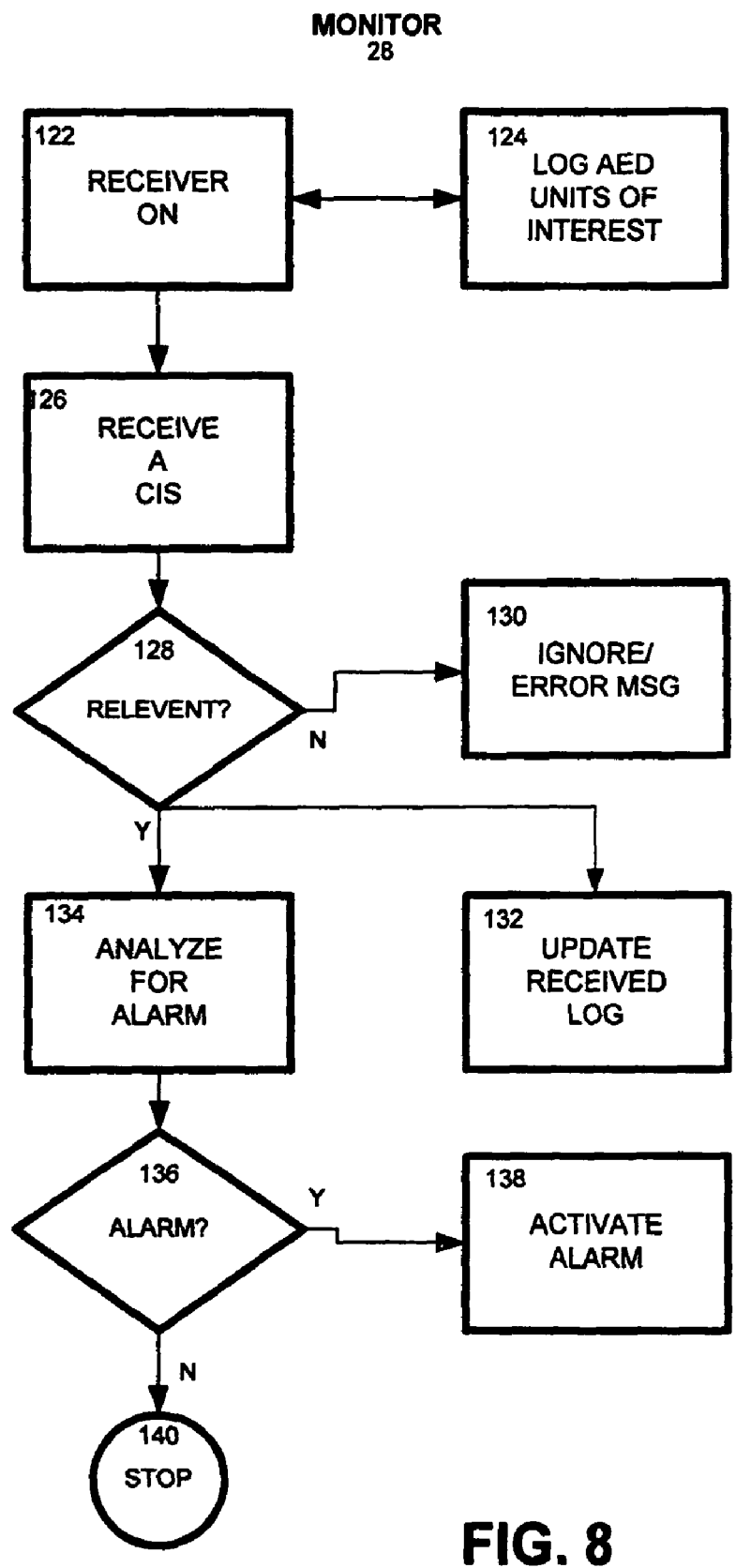
FIG. 8 is a logic flow diagram illustrating exemplary steps for processing a condition information stream.

Continuing with FIG. 8, the monitor 28 has a constant on (24 hours per day 7 days a week) receiver 67, step 122. The receiver 67 stands ready to receive a condition information stream 24. In addition, the programming of the monitor 28 may be programmed to know which PEDs 12 it is monitoring, step 124. This knowledge may be based on knowing the PED's serial number.

Upon receiving a condition information stream, step 126, the programming in the monitor 28 checks, step 128, the log of PED units of interest to confirm it is a PED 12 being monitored by this monitor. If it is not, it is ignored, or an error may be reported, step 130. If it is, the condition information stream 24 is stored in the receiver log, step 132, and decoded and analyzed to determine if it contains alert information, step 134. If alert information is detected (e.g., an ASI Status 24G, or defibrillator error code 24H indicating a problem), step 136, the proper sensory alert 74 is activated, step 134.

The steps shown in FIGS. 7 and 8 are for the AUTO-TEST Mode. As those skilled in the art will appreciate, the steps for other self-diagnostic test modes, such as self-diagnostic tests and startup self-diagnostic testing in an ON condition, are similar. More specifically, the other self-diagnostic test modes should result in the transmission of a condition information stream. The primary differences, however, are that the self-diagnostic testing will not be started by the clock; it should not result in disrupting the AUTO-TEST (e.g., increasing the index counter, step 120); and the specific self-diagnostic test is pre-determined (e.g., not determined by the Main Processor).

Figure 9:
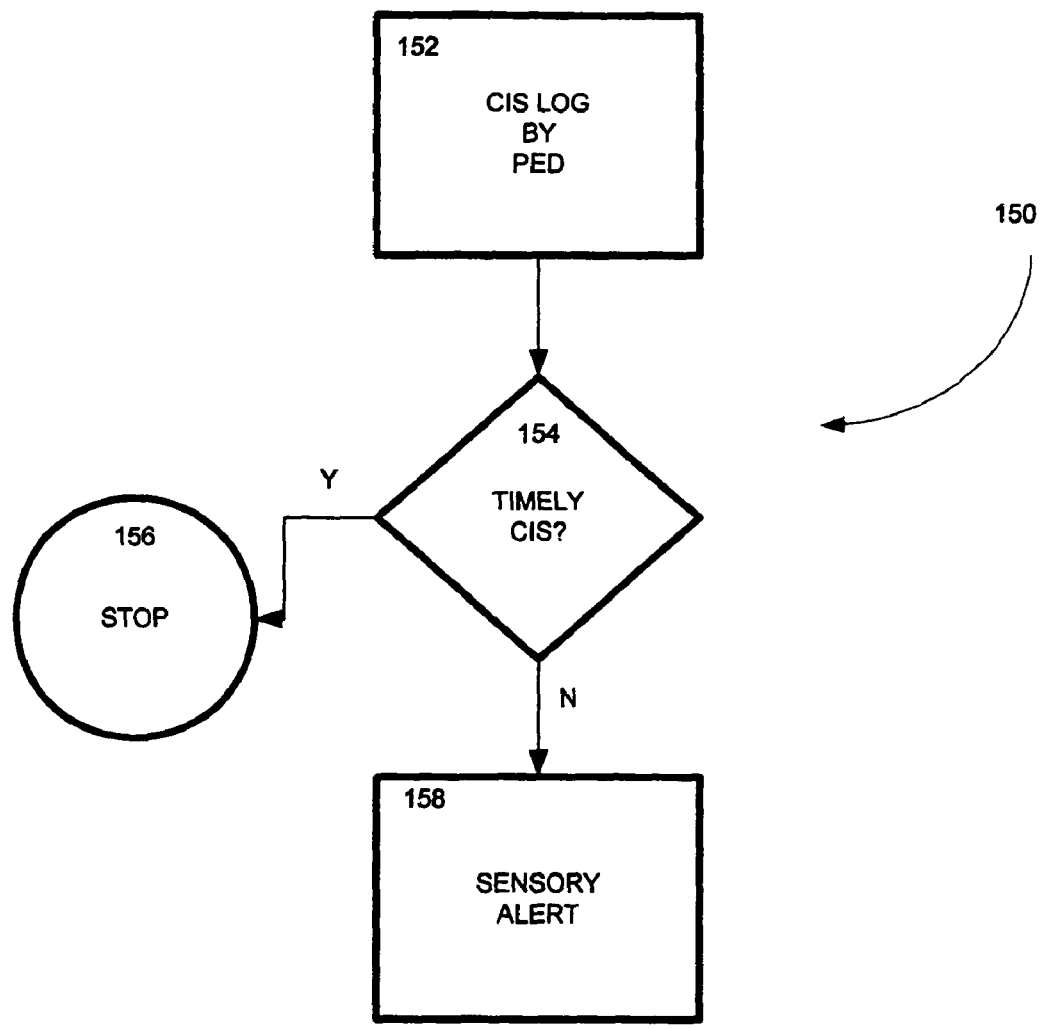
FIG. 9 is a logic flow diagram illustrating exemplary steps for providing an alert when a monitor fails to receive an expected condition information stream.

As shown in FIG. 9, the monitor 28 programming may include a subroutine (generally referred to by reference number 150) which determines whether a condition information stream from a particular broadcast transmitter 22 has not been received in a timely fashion. In step 152, the monitor's programming (most likely in memory) has a log of when to expect a particular condition information stream. Based on this log, the monitor's computer programming looks to confirm receipt of an expected conditional information stream. If the expected conditional information stream has been received, the subroutine is simply terminated, step 156. If not, the monitor 28 issues an alert, step 158.

More specifically, it is desirable that each PED 12 conduct AUTO-TEST self-diagnostic tests on a periodic interval (e.g., every 24 hours). Thus, these self-diagnostic tests should generate a condition information stream 24 at least every 24 hours. The monitor 28 thus should have knowledge that at least one condition information stream 24 should be received from a particular broadcast transmitter 22 every 24 hours, within some reasonable tolerance. In the event a condition information stream 24 is not received in a timely fashion, the monitor's programming should activate an alert.

Figure 10:
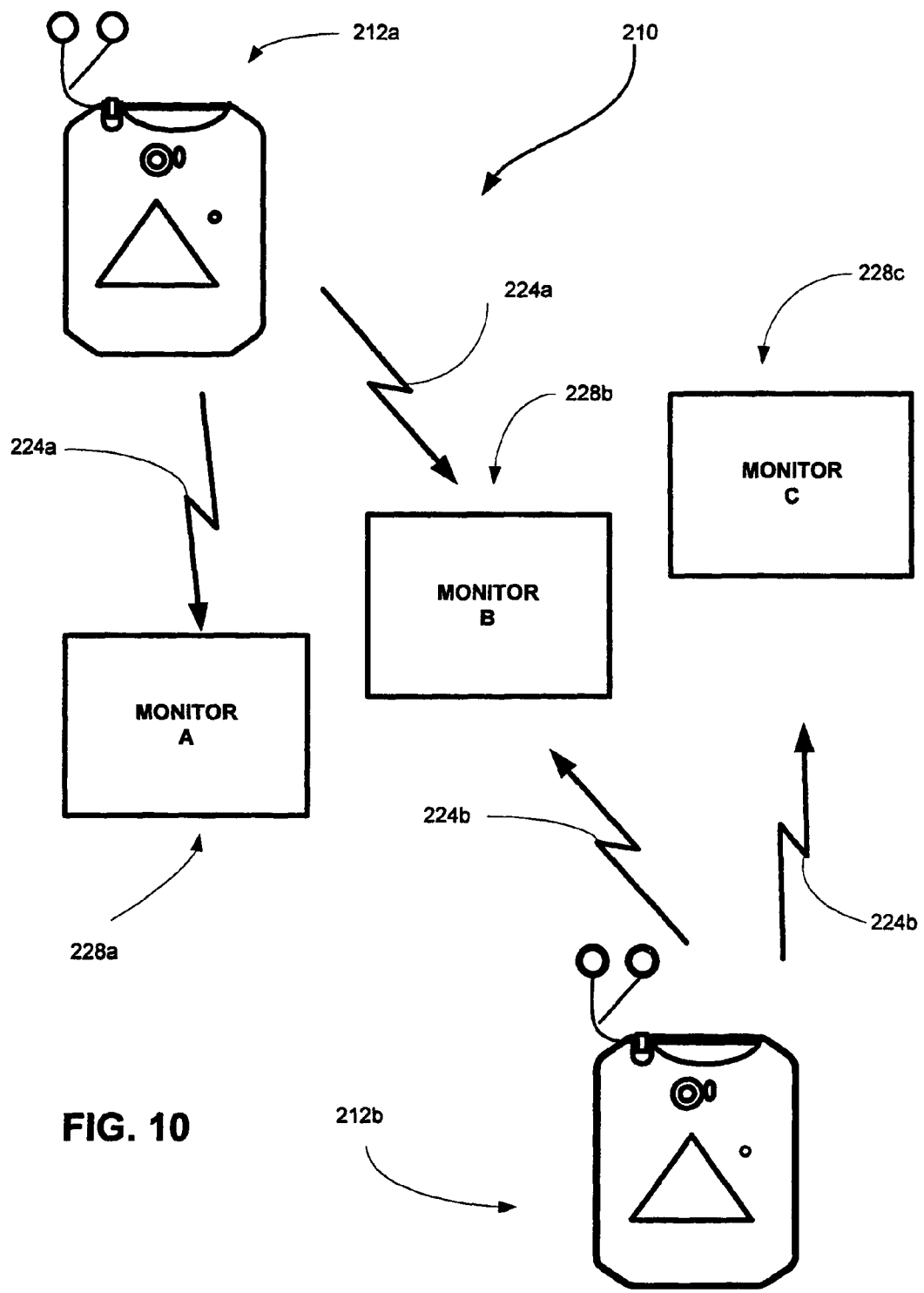
FIG. 10 illustrates a plan view of an enhanced system according to one exemplary embodiment of the invention.

FIG. 10 is an enhanced version of the system 210 depicted in FIG. 1. In this enhanced version, like components are given the same reference number preceded by the number 2. In this enhanced system 210, there are multiple monitors 228 for receiving a given condition information steam 224 from a given PED 212a. Depending upon information in the data payload 64 (see FIG. 3), the multiple monitors could perform several services. It should be appreciated that each monitor 228 if in range of the PED 212a will receive the condition information stream 224, thus the flexibility of the enhanced system 210 is based on how each monitor 228 acts upon the condition information stream.

In the most basic enhanced system 210, each monitor 228 is identical. In other words, each monitor 228 receives the condition information stream 224 and analyzes the condition information stream in the same way. In reality, one monitor 228 is backing up the other.

In another alternative, the monitors 228 are programmed to handle the same condition information stream 224 in different ways. For example, one monitor 228a may be located in a maintenance area and another monitor 228b may be located in a medical area. Thus, when the condition information stream 224 contains information indicating a requirement for maintenance, only monitor 228a alerts. However, when the condition information stream 224 indicates a rescue attempt, the other monitor 228b alerts. The ability of the programming in the monitor 228 to distinguish between a maintenance event and a rescue attempt could be accomplished by evaluating the event code 24I in the data payload 64. (See FIG. 3).

In yet another enhancement, some monitors 228 could be programmed to work with more than one PED 212. In the illustrative example, all condition information streams 224 are acted upon by the medical monitor 228b if the condition information stream contains information indicating a rescue attempt. However, for non-medical condition information streams, monitor 228a reacts to condition information stream 224A from one PED 212a, and monitor 228c reacts to condition information stream 224B from the other PED 212b. It should be appreciated that repeaters 88 may be incorporated into this enhanced system 210.

Alternate embodiments of the monitoring system will become apparent to one of ordinary skill in the art to which the present invention pertains without departing from its spirit and scope. In particular, those skilled in the art will recognize alternate circuitry and programming. Thus, although this invention has been described in exemplary form with a certain degree of particularity, it should be understood that the present disclosure has been made only by way of example and that numerous changes in the details of construction and the combination and arrangement of parts or steps may be resorted to without departing from the spirit or scope of the invention. Accordingly, the scope of the present invention is defined by the appended claims rather than the foregoing description.

What is claimed is:

1. A system for monitoring a portable emergency medical device, comprising;
    a portable emergency medical device including
        a broadcast transmitter, the broadcast transmitter capable of broadcasting a condition information stream;
        device programmable circuitry programmed with a self-diagnostic test, having programming to execute the self-diagnostic test, to generate the condition information stream containing a data payload based on the executed self-diagnostic test containing status information, and using the broadcast transmitter, transmit the condition information stream; and
    a remote monitor including
        a broadcast receiver, the broadcast receiver capable of receiving from the broadcast transmitter the condition information stream,
        a monitor having programmable circuitry with programming thereon to analyze the information in the condition information stream and to determine if the status information therein warrants a sensory alert or not, and
        a sensory alert that may be activated by the programming of the monitor programmable circuitry
    wherein the broadcast receiver and broadcast transmitter are not networked.

2. The system of claim 1 wherein the programming of the device programmable circuitry further includes programming to execute the self-diagnostic test periodically, and the programming of the monitor programmable circuitry includes programming to determine if a condition information stream was timely received based on the periodicity of self-diagnostic tests and issue an alert if it was not.

3. The system of claim 1 wherein the programming of the monitor programmable circuitry includes the capability of determining whether more than a known period has passed since receipt of the last condition information stream and issue an alert if so.

4. The system of claim 1 wherein the portable emergency medical device is a portable external defibrillator.

5. The system of claim 1 wherein the transmitting programming converts the condition information stream into line code.

6. The system of claim 5 wherein the transmitting programming further includes programming to broadcast the line code by turning the broadcast transmitter on and off.

7. The system of claim 1 wherein the programmable circuitry has a control circuit controlled by the programming for turning the broadcast transmitter ON to broadcast the condition information stream and turning the broadcast transmitter OFF after the broadcast.

8. The system of claim 5 wherein the line code does not contain a separate clock signal.

9. The system of claim 5 wherein the line code has bits and each bit is of the same time duration.

10. The system of claim 1 further including a repeater, the repeater being between the portable emergency medical device and the monitor.

11. The system of claim 1 wherein the system includes at least one more portable emergency medical device than monitor.

12. The system of claim 1 wherein the system includes two monitors and the programming in each monitor allows each monitor to receive and analyze the condition information stream from the same portable emergency medical device.

13. The system of claim 12 wherein the condition information stream contains information to permit each monitor to react differently.

14. The system of claim 12 wherein the system includes two portable emergency medical devices and three monitors, and the first monitor receives and analyzes condition information streams from both portable emergency medical devices, the second monitor receives and analyzes a condition information stream only from one portable emergency medical device and the third monitor receives and analyzes a condition information stream only from the other portable emergency medical device.

15. A portable emergency medical device including:
programmable circuitry and programming for performing a medical procedure;
self-diagnostic test programming executing within the programmable circuitry outputting a condition information stream;
a self-contained broadcast transmitter electrically associated with the programmable circuitry for broadcasting the condition information stream to a non-networked remote broadcast receiver; and
a portable power source powering the portable emergency medical device and the broadcast transmitter.

16. The portable emergency medical device of claim 15 wherein the medical procedure is defibrillation.

17. The portable emergency medical device of claim 15 wherein the programmable circuitry has a control circuit controlled by the programming for turning the broadcast transmitter ON to broadcast the condition information stream and turning the broadcast transmitter OFF after the broadcast.

18. The portable emergency medical device of claim 17 wherein the transmitter is of the type that broadcasts by turning itself on and off.

19. The portable emergency medical device of claim 15 wherein the transmitter produces a signal that does not contain a clock signal.

20. A method for transmitting status information of a portable emergency medical device to a remote monitor comprising the steps of:
A) obtaining a portable emergency medical device, having a broadcast transmitter therein, and capable of performing a self-diagnostic test;
B) conducting the self-diagnostic test to determine an operational status;
C) converting the operational status into a condition information stream;
D) using the broadcast transmitter to broadcast the condition information stream to a remote non-networked broadcast receiver;
E) turning OFF the broadcast transmitter.

21. The method of claim 20 wherein for the obtained portable emergency medical device, steps B-E are repeated.

22. The method of claim 21 wherein in the repeated step C, each condition information stream is unique.

23. The method of claim 20 wherein in the step of conducting a self-diagnostic test, the self self-diagnostic test is conducted sua sponte.

24. The method of claim 20 wherein in the step of conducting a self-diagnostic test, the self self-diagnostic test is manually activated.

25. A method of alerting a user to the operational condition of a portable emergency medical device comprising the steps of:
A) obtaining a portable emergency medical device, having a broadcast transmitter therein, and capable of performing a self-diagnostic test;
B) obtaining a remote monitor having a broadcast receiver capable of receiving a signal from the broadcast transmitter and having programming to analyze the signal and activate a sensory alert;
C) conducting the self-diagnostic test on the portable emergency medical device to determine an operational status;
D) converting the operational status into a condition information stream;
E) using the broadcast transmitter to broadcast the condition information stream, the broadcast transmitter and broadcast receiver not being networked;
F) using the broadcast receiver in the monitor to receive the broadcasted condition information stream;
G) when received by the monitor, analyzing the condition information stream to determine the operational status; and
H) activating the sensory alert if appropriate.

26. The method of claim 25 further including the step of repeating the steps C-H for the obtained portable emergency medical device but generating in step D a unique condition information stream each time the steps are repeated thereby creating multiple unique condition information streams from a single broadcast transmitter.

27. The method of claim 26 wherein each unique condition information stream contains a unique segment having an ordinal value, and further including a step I, occurring between steps F and G, of the broadcast receiver analyzing a latest unique condition information stream as to the penultimate unique condition information stream to determine if there is a missed unique condition information stream.

28. The method of claim 25 wherein in the step of obtaining a portable emergency medical device, the device includes a defibrillator.

29. The method of claim 25 wherein in the step of conducting a self-diagnostic test, the self self-diagnostic test is conducted sua sponte.

30. The method of claim 25 wherein in the step of conducting a self-diagnostic test, the self self-diagnostic test is manually activated.

31. A method of alerting a user to the operational condition of a portable emergency medical device comprising the steps of:
A) obtaining a portable emergency medical device, having a broadcast transmitter therein and programming to transmit an intermittent signal, the broadcast transmitter being powered by a power source self-contained within the portable medical device;
B) obtaining a monitor that is separate from the portable emergency medical device and having a broadcast receiver capable of receiving the intermittent signal from the broadcast transmitter when the broadcast transmitter and broadcast transmitter are not networked and having programming knowledgeable of when the intermittent signal should be received; and activate a sensory alert;
C) activating the sensory alert if the periodic signal is not received when anticipated.

32. The method of claim 31 wherein in step A, the intermittent signal contains the results from a self-diagnostic test.

* * * * *